(12) United States Patent
Anderson (10) Patent No.: US 9,636,236 B2
(45) Date of Patent: May 2, 2017

(54) HANDLE ASSEMBLY GRIPPING DEVICE

(71) Applicant: Biomet Manufacturing, LLC, Warsaw, IN (US)

(72) Inventor: David Anderson, Winona Lake, IN (US)

(73) Assignee: Biomet Manufacturing LLC, Warsaw, IN (US)

( * ) Notice: Subject to any disclaimer, the term of this patent is extended or adjusted under 35 U.S.C. 154(b) by 1036 days.

(21) Appl. No.: 13/875,591

(22) Filed: May 2, 2013

(65) Prior Publication Data
US 2014/0330324 A1   Nov. 6, 2014

(51) Int. Cl.
*A61B 17/68*   (2006.01)
*A61F 2/46*    (2006.01)
*A61B 17/88*   (2006.01)

(52) U.S. Cl.
CPC ........ *A61F 2/4606* (2013.01); *A61B 17/8872* (2013.01)

(58) Field of Classification Search
CPC .............. A61F 2/461; A61F 2002/4615; A61F 2002/462; A61F 2002/4625; A61F 2002/4629; B25B 5/04; B25B 5/067; B25B 5/082; B25B 5/125; B25B 7/00; B25B 9/00; B25B 13/28; B25B 3/00
USPC .................. 269/3, 6, 95; 294/99.2
See application file for complete search history.

(56) References Cited

U.S. PATENT DOCUMENTS

| | | | | |
|---|---|---|---|---|
| 4,841,819 A | * | 6/1989 | Williams | B25B 9/02 29/278 |
| 5,387,019 A | * | 2/1995 | Britzke, II | B25B 9/02 294/2 |
| 6,562,074 B2 | * | 5/2003 | Gerbec | A61F 2/4455 623/17.15 |
| 6,648,917 B2 | * | 11/2003 | Gerbec | A61F 2/4455 623/17.11 |
| 7,384,086 B2 | * | 6/2008 | Lukaszynski | H01H 85/0208 29/278 |
| 8,777,287 B2 | * | 7/2014 | Ludwig | B25J 1/04 294/111 |
| 8,986,307 B2 | * | 3/2015 | Kirschman | A61F 2/4465 606/86 A |
| 9,004,563 B2 | * | 4/2015 | Buzby | A47F 13/06 294/115 |

* cited by examiner

*Primary Examiner* — Anu Ramana
(74) *Attorney, Agent, or Firm* — Schwegman Lundberg & Woessner, P.A.

(57) ABSTRACT

An orthopedic handle gripping assembly comprising: an elongated shaft having a proximal section and a distal section opposite thereof along a longitudinal axis of the shaft; a hub portion proximate the distal section of the shaft; a gripping member contiguous with the hub portion and having a first jaw and a second jaw, the first and second jaws being separated by a predefined distance to thereby form a central opening for receiving an orthopedic component that is to be gripped by the gripping member; a handle coupled to and extending from the gripping member; and a slot formed into the hub portion, the slot being configured to allow at least a portion of the handle to be manually biased towards the elongated shaft to thereby increase the predefined distance between the first and second jaws.

18 Claims, 5 Drawing Sheets

HANDLE ASSEMBLY GRIPPING DEVICE

TECHNICAL FIELD

The present teachings are related to a handle assembly for gripping an object, and more particularly to a handle assembly for gripping an orthopedic component.

BACKGROUND OF THE DISCLOSURE

The statements in this section merely provide background information related to the present disclosure and should not be construed as constituting prior art.

Many portions of the human anatomy naturally articulate relative to one another. Generally, the articulation of these anatomic regions is smooth and non-abrasive in nature, particularly in the presence of natural tissues, such as cartilage and strong bone.

Over time, however, due to injury, stress, degenerative health problems and various other issues, the ease by which these anatomic regions are able to articulate degenerates in quality, thereby leaving the articulation of these anatomic regions abrasive and impractical. For example, injury may cause the cartilage or the bony structure to become weak, damaged, or even non-existent. As a result, the natural articulation of these anatomical regions is no longer possible for these affected individuals.

At such times, it may be desirable to replace the affected anatomical regions with a prosthetic component or other such biomedical implant device so that normal articulation may be restored. To replace the affected anatomical region with a prosthetic component or implant device, various instruments for inserting, positioning and/or impacting the device within the anatomical region of interest may be used as part of the orthopedic procedure. While several different types of instruments are commercially available to accomplish these tasks, many of these devices are relatively large in size, not to mention difficult to assemble and to operate, particularly as many of these devices are limited by ergonomic shortcomings. Moreover, many of these devices are difficult to clean/sterilize, thereby leaving hospitals frustrated with trying to validate and pass the short sterilization and cleaning cycles mandated by the FDA. As such, there is a need to provide an improved and reusable implant insertion device that addresses one or more of these known deficiencies within the art.

SUMMARY OF THE DISCLOSURE

In accordance with one aspect of the present application, an orthopedic handle gripping assembly in provided. According to this aspect of the present application, the orthopedic handle gripping assembly comprises an elongated shaft having a proximal section and a distal section opposite thereof along a longitudinal axis of the shaft; a hub portion proximate the distal section of the shaft; a gripping member contiguous with the hub portion and having a first jaw and a second jaw, the first and second jaws being separated by a predefined distance to thereby form a central opening for receiving an orthopedic component that is to be gripped by the gripping member; a handle coupled to and extending from the gripping member; and a slot formed into the hub portion, the slot being configured to allow at least a portion of the handle to be manually biased towards the elongated shaft to thereby increase the predefined distance between the first and second jaws.

According to another aspect of the present application, the orthopedic handle gripping assembly comprises an elongated shaft having a proximal section and a distal section opposite thereof along a longitudinal axis of the shaft; a hub portion proximate the distal section of the shaft; a gripping member contiguous with the hub portion and having a first jaw and a second jaw, the first and second jaws being separated by a predefined distance to thereby form a central opening for receiving an orthopedic component that is to be gripped by the gripping member; a first handle coupled to and extending from the gripping member, the first handle being substantially parallel to the elongated shaft; a second handle coupled to and extending from the gripping member, the second handle being substantially parallel to the first handle; a first slot formed into the hub portion, the first slot being configured to allow at least a portion of the first handle to be manually biased towards the elongated shaft; and a second slot formed into the hub portion, the second slot being configured to allow at least a portion of the second handle to be manually biased towards the elongated shaft.

In accordance with still another aspect of the present application, a method of gripping an orthopedic component as part of an orthopedic procedure is provided. According to this aspect of the present application, the method comprises the steps of: providing an orthopedic handle gripping assembly comprising: an elongated shaft having a proximal section and a distal section opposite thereof along a longitudinal axis of the shaft; a hub portion proximate the distal section of the shaft; a gripping member contiguous with the hub portion and having a first jaw and a second jaw, the first and second jaws being separated by a predefined distance to thereby form a central opening; a handle coupled to and extending from the gripping member; and a slot formed into the hub portion; manually biasing the handle towards the elongated shaft from a first position to a second position; placing the orthopedic component within the central opening of the gripping member as the handle is being biased towards the elongated shaft; and causing the handle to return to the first position to thereby grip the orthopedic component with the first and second jaws.

Still other objects and benefits of the application will become apparent from the following written description along with the accompanying figures.

BRIEF DESCRIPTION OF THE DRAWINGS

The above-mentioned aspects of the present application and the manner of obtaining them will become more apparent and the teachings of the present application itself will be better understood by reference to the following description of the embodiments of the present application taken in conjunction with the accompanying drawings, wherein.

Corresponding reference characters indicate corresponding parts throughout the several views. Although the exemplification set out herein illustrates embodiments of the present application, in several forms, the embodiments disclosed below are not intended to be exhaustive or to be construed as limiting the scope of the present application to the precise forms disclosed.

DETAILED DESCRIPTION

The embodiments of the present application described below are not intended to be exhaustive or to limit the teachings of the present application to the precise forms disclosed in the following detailed description. Rather, the embodiments are chosen and described so that others skilled in the art may appreciate and understand the principles and practices of the present application.

Unless defined otherwise, all technical and scientific terms used herein have the same meaning as commonly understood by one of ordinary skill in the art to which this application belongs. Although any method and materials similar or equivalent to those described herein can be used in the practice or testing of the present application, the specific methods and materials are now described.

Figure 1:
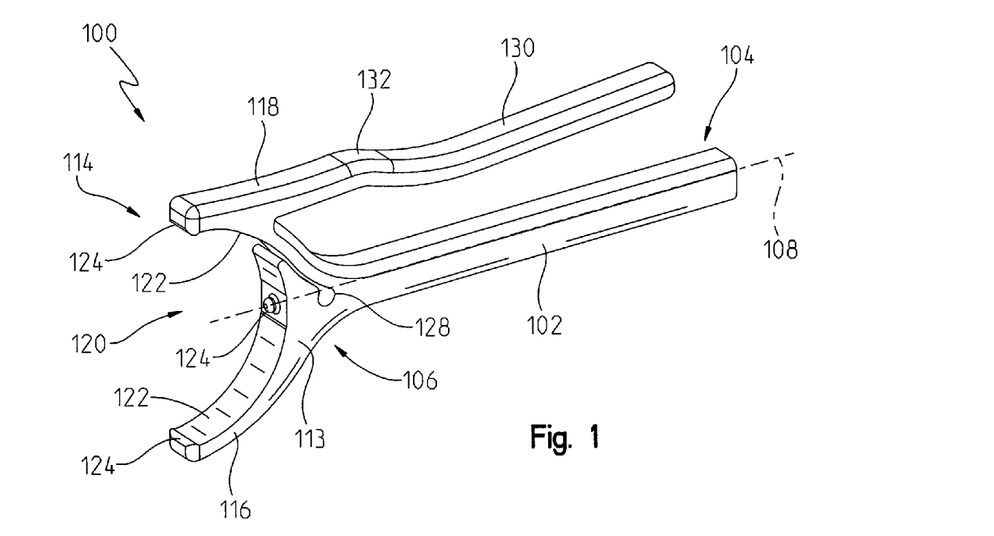
FIG. 1 represents a perspective view of an illustrative handle gripping assembly in accordance with the teachings of the present disclosure.
Figure 2:
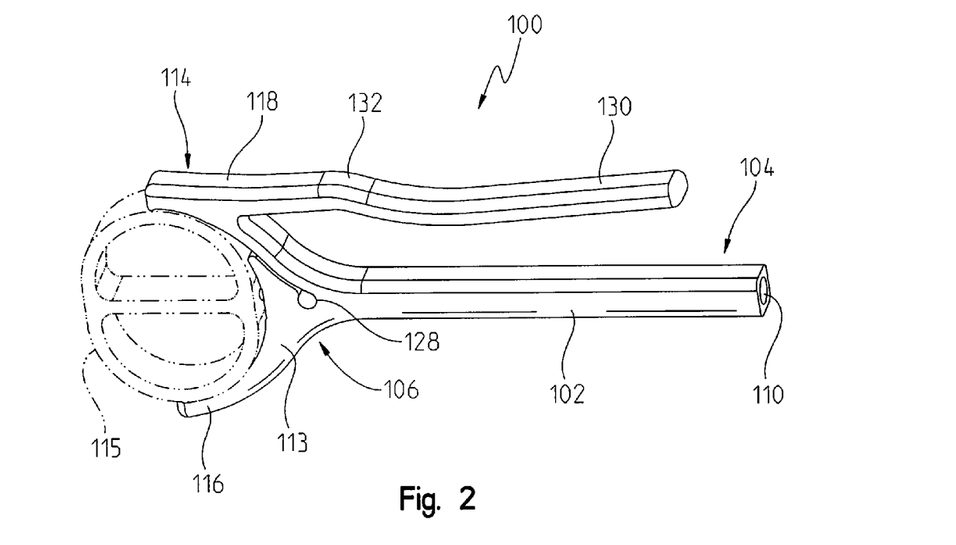
FIG. 2 represents a perspective view of the illustrative handle gripping assembly of FIG. 1 grasping an implant component.
Figure 3:
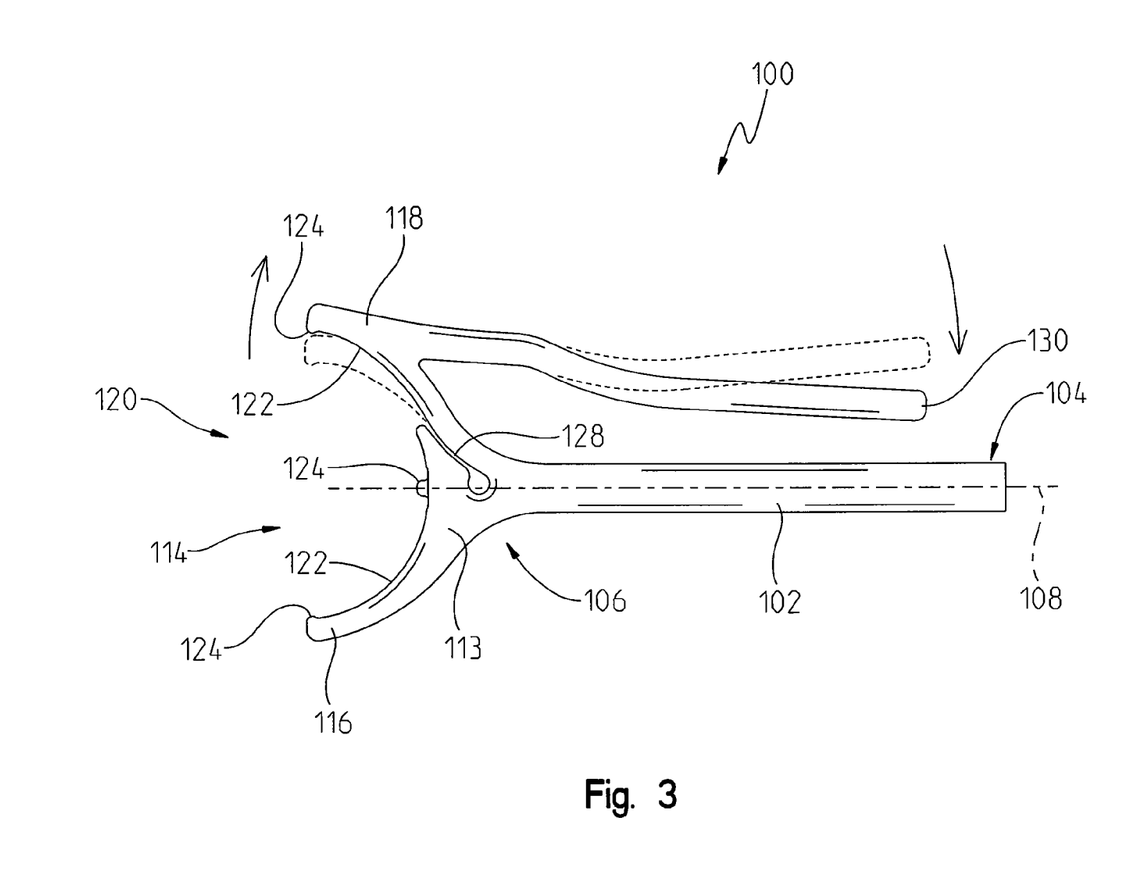
FIG. 3 represents a side view of the illustrative handle gripping assembly of FIG. 1, the illustration depicting a portion of the assembly in phantom lines to demonstrate the associated movement of the assembly during actuation.

Referring to FIGS. 1-3, an illustrative handle gripping assembly 100 is provided in accordance with certain aspects the present teachings. According to this embodiment, the handle gripping assembly 100 comprises an elongated shaft 102 having a proximal section 104 and a distal section 106 opposite thereof along a longitudinal axis 108 of the handle assembly 100. The proximal section 104 of the elongated shaft 102 may further comprise a bore 110 that is configured to releasably receive the chuck 112 of a corresponding orthopedic driver handle (see FIG. 6, for instance). It should be understood and appreciated herein that while the use of a driver handle is optional in accordance with the present disclosure, attaching a driver to the handle assembly 100 may be particularly useful for reaching anatomical regions of a patient that would otherwise be difficult to reach.

Proximate to the distal section 106 of the elongated shaft 102 is a hub portion 113 that contiguously branches into gripping member 114 defined by a first substantially arcuate jaw 116 and a second substantially arcuate jaw 118. The jaws 116, 118 are spaced apart from one another by a suitable amount to define a central opening 120 and together form an engagement surface 122 that is adapted to at least partially mate with an object placed therein. In other words, the engagement surface 122 formed by the jaws 116, 118 is designed to physically contact, and at least partially conform to, an object that is placed within the central opening 120 and into the gripping member 114. While not required herein, in accordance with certain aspects of the present disclosure, the engagement surface 122 may also include one or more raised contact surfaces or pegs 124 that are adapted to physically mate with or contact the object of interest. According to certain specific aspects of the present disclosure, and as is illustratively shown in FIG. 1, three raised contact surfaces 124 may be utilized to form a tripod-like configuration that is adapted to stabilize and enhance the gripping attributes of the jaws 116, 118 as an object is placed therein. An illustrative example of an implant component 115 being gripped by the jaws 116, 118 in accordance with one aspect of the present teachings is shown in FIG. 2.

To allow the jaws 116, 118 to be compressed or actuated so that an object can be gripped in accordance with the teachings of the present disclosure, a blind slot 128 is formed into the engagement surface 122 of the hub portion 113 along a direction intersecting the longitudinal axis 108. In accordance with certain aspects of the present disclosure, the blind slot 128 intersects the longitudinal axis 108 at an angle of about 45°.

Extending from the second jaw 118 in a substantially parallel manner to the elongated shaft 102 is a handle 130 that is configured to be actuated by a user in order to grip an object with the gripping member 114. As is illustratively shown in FIG. 3, at least a portion of the handle 130 is configured to be biased towards the elongated shaft 102, such biasing movement being accomplished by way of the blind slot 128, which is optimized to allow handle compression upon squeezing the handle 130 and the elongated shaft 102 towards one another (as indicated by the arrows of FIG. 3). In particular, the blind slot 128 allows the handle 130 to be displaced by way of elastic deformation such that when the handle 130 is pressed downwards towards the elongated shaft 102, the second jaw 118 is biased away from the first jaw 116, thereby resulting in an increased dimensional area of the central opening 120 so that an object can be received therein. Once the object is placed within the central opening 120 and against the engagement surface 122, the act of releasing the handle 130 will cause the second jaw 118 to return or decompress to its original position such that the object is grasped within the gripping member 114.

Figure 4:
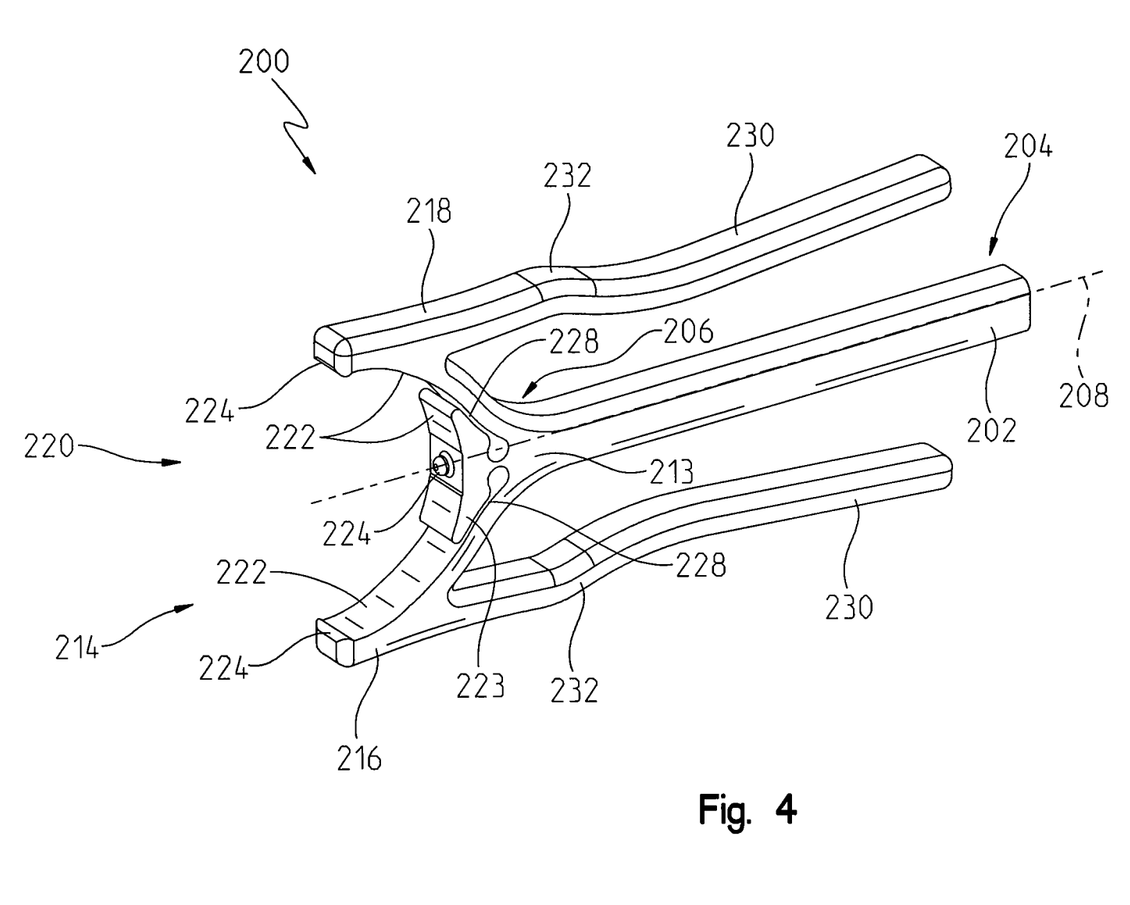
FIG. 4 represents a perspective view of another illustrative handle gripping assembly in accordance with the teachings of the present disclosure.
Figure 5:
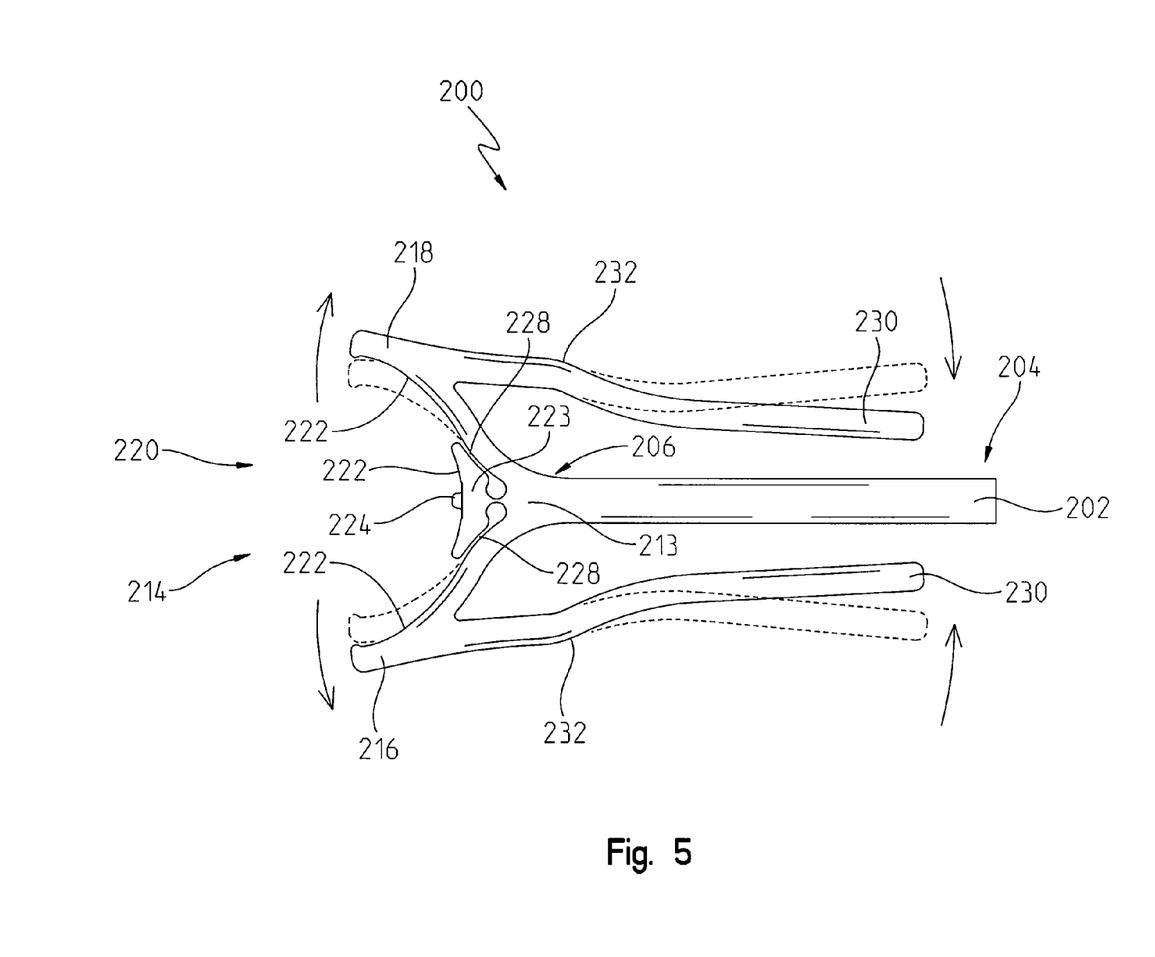
FIG. 5 represents a side view of the illustrative handle gripping assembly of FIG. 4, the illustration depicting a portion of the assembly in phantom lines to demonstrate the associated movement of the assembly during actuation.

Referring to FIGS. 4-5, another illustrative handle gripping assembly 200 is provided in accordance with certain aspects the present teachings. According to this embodiment, the handle gripping assembly 200 comprises an elongated shaft 202 having a proximal section 204 and a distal section 206 opposite thereof along a longitudinal axis 208 of the handle assembly 200. The proximal section 204 of the elongated shaft 202 may further comprise a bore (not shown) that is configured to releasably receive the chuck of a corresponding orthopedic driver handle. It should be understood and appreciated herein that while the use of a driver handle is optional in accordance with the present disclosure, attaching a driver to the handle assembly 200 may be particularly useful for reaching anatomical regions of a patient that would otherwise be difficult to reach.

Proximate to the distal section 206 of the elongated shaft 202 is a hub portion 213 that contiguously branches into a gripping member 214 defined by a first substantially arcuate jaw 216 and a second substantially arcuate jaw 218. The jaws 216, 218 are spaced apart from one another by a suitable amount to define a central opening 220 and together form an engagement surface 222 that is adapted to at least partially mate with an object placed therein. In other words, the engagement surface 222 formed by the jaws 216, 218 is designed to physically contact, and at least partially conform to, an object that is placed within the central opening 220 and into the gripping member 214.

In accordance with certain aspects of the present disclosure, the engagement surface 222 may also include an elevated platform 223 that is adapted to physically mate with or contact the object of interest together with the jaws 216, 218. According to this aspect of the present disclosure, one or more raised contact surfaces or pegs 224 may also be added to the engagement surface 222 to stabilize and enhance the gripping attributes of the jaws 216, 218 and elevated platform as an object is placed therein.

To allow the jaws 216, 218 to be actuated so that an object can be gripped in accordance with the teachings of the present disclosure, a pair of blind slots 228 are formed into the engagement surface 222 of the hub portion 213 along a direction intersecting the longitudinal axis 208. In accordance with certain aspects of the present disclosure, each of the blind slots 228 intersects the longitudinal axis 208 at an angle of about 45°.

Respectively extending from each of the first and second jaws 216, 218 in a substantially parallel manner to the elongated shaft 202 are handles 230 that are configured to be actuated by a user in order to grip an object with the gripping member 214. As is illustratively shown in FIG. 5, at least a portion of the handles 230 are configured to be biased towards the elongated shaft 202, such biasing movement being accomplished by way of the blind slots 228, which are optimized to allow handle compression upon squeezing the handles 230 towards one another (as indicated by the arrows of FIG. 5). In particular, the blind slots 228 allow the handles 230 to be displaced by way of elastic deformation such that when the handles 230 are squeezed towards one another, the first and second jaws 216, 218 are biased away from one another, thereby resulting in an increased dimensional area of the central opening 220 so that an object can be received therein. Once the object is placed within the central opening 220 and against the engagement surface 222, the act of releasing the handles 230 will cause the first and second jaws 216, 218 to return to their respective original positions such that the object is grasped within the gripping member 214.

Those of skill in the art should understand and appreciate herein that the shape of any of the disclosed handles 130, 230 may be modified to accommodate the grip of the user. For instance, any of the handles 130, 230 can be manufactured with smooth corners and/or other surfaces to reduce any handling discomfort, as well as may include one or more roughened finger portions, ridges and/or grooves to enhance the gripability of the assemblies 100, 200. In accordance with certain aspects of the present disclosure, one or more of the handles 130, 230 may include an indented groove 132, 232 to provide a surface for the user's thumb to grip during a gripping procedure. While not shown specifically herein, the indented groove or grooves 132, 232 may further include bumps, ridges and/or other such ribbing effect on its surface to further improve the grip of the user's thumb if desired.

It should be understood and appreciated herein that the gripping members 114, 214 can be designed to overlap the object for extra stability if desired. Moreover, in accordance with certain aspects of the present disclosure, one or both of the engagement points defined by the jaws may be deviated towards the gripped object so that a clamp preload is present, thereby enhancing the gripping properties of the gripping members 114, 214.

In terms of the length, size and angular orientation of the slots 128, 228, it should be understood and appreciated herein that these various properties can be modified as desired in accordance with the targeted use for the gripping assemblies. In accordance with certain aspects of the present invention, for instance, the length of the slots 128, 228 may be configured such that they terminate a certain distance from the pivot point of the assembly to thereby allow the handles 130, 230 to be actuated with very little hand force applied thereto by the user (e.g., about 5 to 10 pounds of hand force).

It should be understood and appreciated herein, that any suitable material may be utilized to fabricate the aforementioned components as long as such components can be reused numerous times without permanently deforming the gripping attributes of the assemblies 100, 200. Such materials include, but are not limited to, titanium, stainless steel, aluminum, brass, plastic, ceramic, as well as any alloys of the foregoing.

Figure 6:
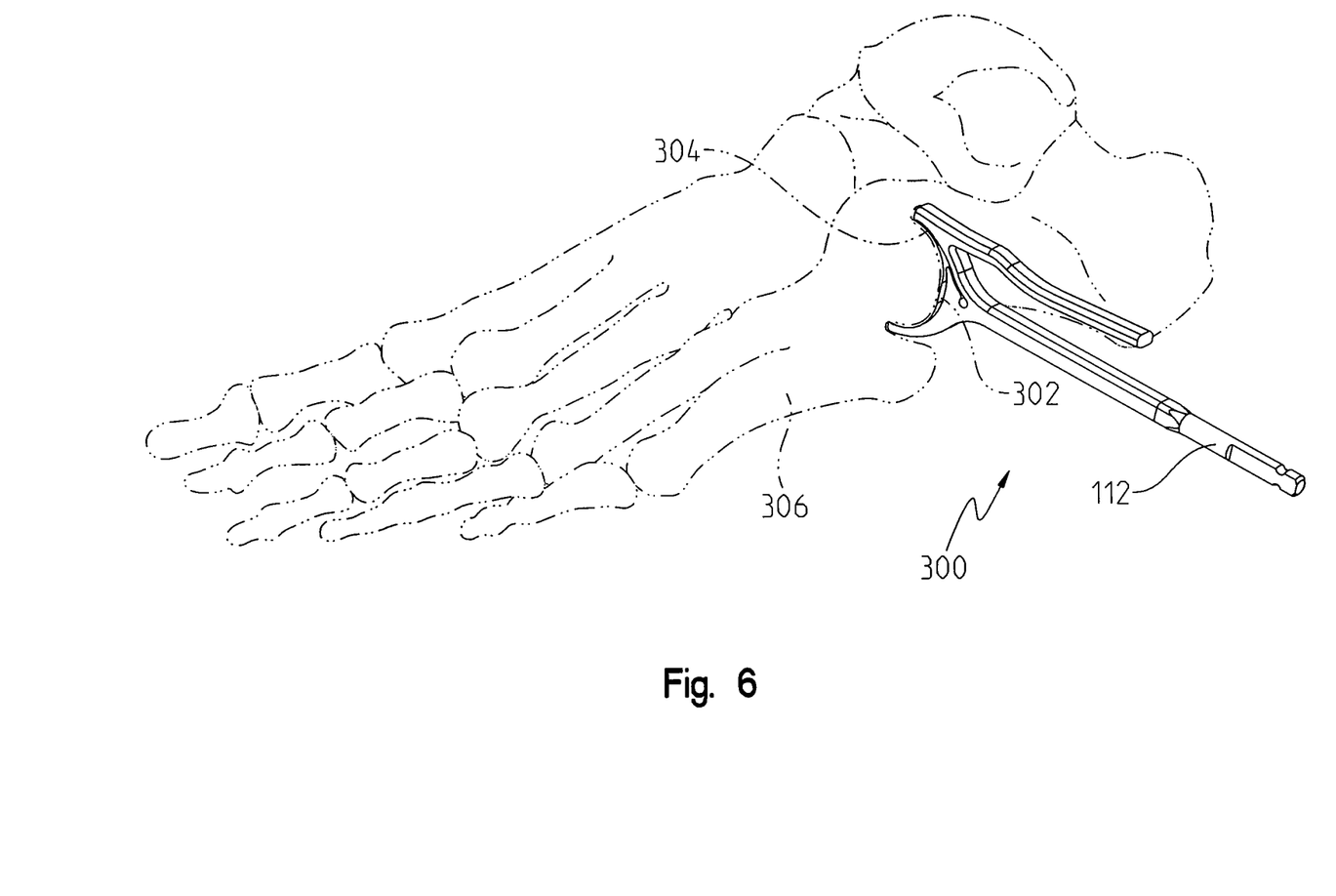
FIG. 6 represents a perspective view of an illustrative handle gripping assembly inserting an implant component during a foot and ankle reconstructive orthopedic procedure in accordance with the teachings of the present disclosure.

Referring now to FIG. 6, an illustrative surgical technique utilizing an illustrative handle gripping assembly 300 in accordance with the teachings of the present disclosure is shown (i.e., the handle gripping assembly 300 is inserting a reconstructive wedge component 302 into an osteotomy cut 304 that has been made in a foot 306). While this specific example illustrates the handle gripping assembly being used as part of a foot/ankle procedure, it should be understood and appreciated herein that those of skill in the art will find it readily apparent that the teachings of the present disclosure can be similarly used with any type of anatomical application. Suitable anatomical applications in which the present teachings can be utilized include, but are not limited to, hip procedures, knee procedures, spinal procedures, shoulder procedures, hand, finger, wrist and elbow procedures and foot, toe and ankle procedures.

While an exemplary embodiment incorporating the principles of the present application has been disclosed hereinabove, the present application is not limited to the disclosed embodiments. Instead, this application is intended to cover any variations, uses, or adaptations of the application using its general principles. Further, this application is intended to cover such departures from the present disclosure as come within known or customary practice in the art to which this present application pertains and which fall within the limits of the appended claims.

The terminology used herein is for the purpose of describing particular illustrative embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms.

These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations).

What is claimed is:

1. An assembly for gripping an orthopedic component, the assembly comprising:
   an elongated shaft extending along a longitudinal axis from a proximal end to a distal end;
   a first jaw extending from the distal end of the shaft;
   a second jaw extending from the distal end of the shaft, the second jaw being separated from the first jaw by a slot that extends into the distal end of the shaft toward the proximal end of the shaft, a distal-facing portion of the first jaw and a distal-facing portion of the second jaw forming a central opening shaped to receive the orthopedic component, the distal-facing portion of the first jaw further including at least one raised contact surface, the raised contact surface positioned at the intersection of the longitudinal axis and an inner surface of the first jaw, the raised contact surface and configured to physically contact the orthopedic component; and
   a handle extending from the second jaw toward the proximal end of the shaft;
   wherein the handle, the slot, and the second jaw are configured such that applying a compressive force between a proximal portion of the handle and a proximal portion of the elongated shaft pivotally increases a separation between the first jaw and the second jaw and thereby widens the central opening.

2. The assembly of claim 1, wherein the first and second jaws together form a substantially arcuate engagement surface for receiving the orthopedic component.

3. The assembly of claim 1, wherein the handle is substantially parallel to the elongated shaft.

4. The assembly of claim 1, wherein the slot extends along an axis that intersects a longitudinal axis of the shaft.

5. The assembly of claim 1, wherein the slot is configured to allow at least the proximal portion of the handle to be manually biased toward the elongated shaft by a compressive force applied to the handle and the elongated shaft.

6. The assembly of claim 1, further comprising a second handle extending from the first jaw toward the proximal end of the shaft.

7. The assembly of claim 6, wherein the second handle is substantially parallel to the elongated shaft.

8. The assembly of claim 1, wherein the orthopedic component is an orthopedic implant.

9. An assembly for gripping an orthopedic component, the assembly comprising:
   an elongated shaft having a proximal section and a distal section opposite thereof along a longitudinal axis of the shaft;
   a hub portion;
   a gripping portion contiguous with the hub portion and having a first jaw and a second jaw, the first and second jaws being separated by a separation to thereby form a central opening for receiving the orthopedic component that is to be gripped by the gripping portion;
   a first handle coupled to and extending from the gripping portion, the first handle being substantially parallel to the elongated shaft;
   a second handle coupled to and extending from the gripping portion, the second handle being substantially parallel to the first handle;
   a first slot formed into the hub portion, the first slot being configured to allow the first handle to change the separation between the first and second jaws; and
   a second slot formed into the hub portion, the second slot being configured to allow the second handle to change the separation between the first and second jaws.

10. The assembly of claim 9, further comprising an elevated platform extending from the hub portion, wherein the first and second jaws together with the elevated platform form a substantially arcuate engagement surface for receiving the orthopedic component.

11. The assembly of claim 9, wherein the engagement surface further comprises at least one raised contact surface adapted to physically contact the orthopedic component.

12. The assembly of claim 9, wherein the first slot extends along an axis that intersects the longitudinal axis of the shaft.

13. The assembly of claim 12, wherein the second slot is a blind slot that intersects the longitudinal axis of the shaft.

14. The assembly of claim 9, wherein the first slot is configured to allow at least a portion of the first handle to be manually biased toward the elongated shaft by a compressive force applied to the first handle and the elongated shaft.

15. The assembly of claim 9, wherein the second slot is configured to allow at least a portion of the second handle to be manually biased toward the elongated shaft by a compressive force applied to the second handle and the elongated shaft.

16. The assembly of claim 9, wherein orthopedic component is an orthopedic implant.

17. An assembly for gripping an orthopedic component, the assembly comprising:
   an elongated shaft extending longitudinally from a proximal end to a distal end;
   a platform extending from the distal end of the shaft;
   a first jaw extending from the distal end of the shaft, the first jaw being separated from the platform by a first slot that extends into the distal end of the shaft toward the proximal end of the shaft;
   a second jaw extending from the distal end of the shaft, the second jaw being separated from the platform by a second slot that extends into the distal end of the shaft toward the proximal end of the shaft, the platform being positioned between the first jaw and the second jaw,
   a distal-facing portion of the first jaw, a distal-facing portion of the second jaw, and the platform forming a central opening shaped to receive the orthopedic component;

a first handle extending from the first jaw toward the proximal end of the shaft; and a second handle extending from the second jaw toward the proximal end of the shaft;

wherein the first handle, the first slot, the second handle, and the second slot are configured such that applying a compressive force between a proximal portion of the first handle and a proximal portion of the second handle pivotally increases a separation between the first jaw and the second jaw and thereby widens the central opening.

18. The assembly of claim 17, wherein the distal-facing portion of the first jaw further includes at least one raised contact surface configured to physically contact the orthopedic component.

* * * * *

UNITED STATES PATENT AND TRADEMARK OFFICE
CERTIFICATE OF CORRECTION

PATENT NO. : 9,636,236 B2
APPLICATION NO. : 13/875591
DATED : May 2, 2017
INVENTOR(S) : David Anderson It is certified that error appears in the above-identified patent and that said Letters Patent is hereby corrected as shown below:

On the Title Page

In item (73), in "Assignee", in Column 1, Line 1, delete "Manufacturing" and insert --Manufacturing,-- therefor Signed and Sealed this
Twenty-second Day of May, 2018

Andrei Iancu
*Director of the United States Patent and Trademark Office*